US006988619B2

(12) United States Patent
Klatt

(10) Patent No.: US 6,988,619 B2
(45) Date of Patent: Jan. 24, 2006

(54) MEDICINAL PRODUCT PACKAGE FOR ERADICATION THERAPY

(75) Inventor: Andreas Klatt, Stockach (DE)

(73) Assignee: Altana Pharma AG, Constance (DE)

( * ) Notice: Subject to any disclaimer, the term of this patent is extended or adjusted under 35 U.S.C. 154(b) by 51 days.

(21) Appl. No.: 10/297,257

(22) PCT Filed: Jun. 23, 2001

(86) PCT No.: PCT/EP01/07148

§ 371 (c)(1),
(2), (4) Date: Dec. 4, 2002

(87) PCT Pub. No.: WO02/00161

PCT Pub. Date: Jan. 3, 2002

(65) Prior Publication Data

US 2003/0136698 A1 Jul. 24, 2003

(30) Foreign Application Priority Data

Jun. 27, 2000 (DE) ................................ 100 30 318

(51) Int. Cl.
*B65D 83/04* (2006.01)
*A61K 9/24* (2006.01)

(52) U.S. Cl. ...................... 206/534; 206/232; 206/499; 424/472; 424/474

(58) Field of Classification Search ........ 206/534–535, 206/459.5, 499, 232, 828; 221/303–310
See application file for complete search history.

(56) References Cited

U.S. PATENT DOCUMENTS

| | | | |
|---|---|---|---|
| 3,308,962 A * | 3/1967 | Bryant | ...................... 211/74 |
| 3,497,982 A | 3/1970 | Schulz | |
| 4,736,849 A | 4/1988 | Leonard et al. | |
| 4,811,845 A * | 3/1989 | Baggett | ...................... 206/534 |
| 4,889,238 A * | 12/1989 | Batchelor | ................... 206/535 |
| 5,265,759 A | 11/1993 | Coffin | |
| 5,542,539 A * | 8/1996 | Early | ......................... 206/499 |
| 5,788,974 A | 8/1998 | D'Amico et al. | |
| 5,945,124 A * | 8/1999 | Sachs et al. | ................ 424/472 |
| 6,158,585 A * | 12/2000 | Labat et al. | ................ 206/372 |
| 6,564,945 B1 * | 5/2003 | Weinstein et al. | .......... 206/531 |

FOREIGN PATENT DOCUMENTS

| | | |
|---|---|---|
| DE | 297 19 070 | 6/1998 |
| DE | 299 13 195 | 3/2000 |
| EP | 0 391 459 | 10/1990 |
| WO | WO 99/02427 | 1/1999 |

OTHER PUBLICATIONS

Huang, J. Q., et al., Treatment after failure: the problem of "non-responders". *Gut* 1999; 45 (Suppl 1): 140-144.

Rubin, Greg P., et al., "The management of *Helicobacter pylori* infection in primary care: Guidelines from the ESPCG". European Journal of General Practice, vol. 5, Sep. 1999, 99-104.

BDA, Künzel, Dolf, BDA-Leitfaden: Unklare Oberbauchbeschwerden; Hrsg. : Kybermed GmbH, Emsdetten, 1. Auflage Emsdetten 1999 (in German).

* cited by examiner

*Primary Examiner*—Bryon Gehman
(74) *Attorney, Agent, or Firm*—Nath & Associates PLLC; Joshua B. Goldberg; Sheldon M. McGee

(57) ABSTRACT

The object of the present invention is to provide a medicinal product package which is suitable for microbe eradication therapy and with which the patient's compliance is increased and thus the result of therapy is improved.

13 Claims, 4 Drawing Sheets

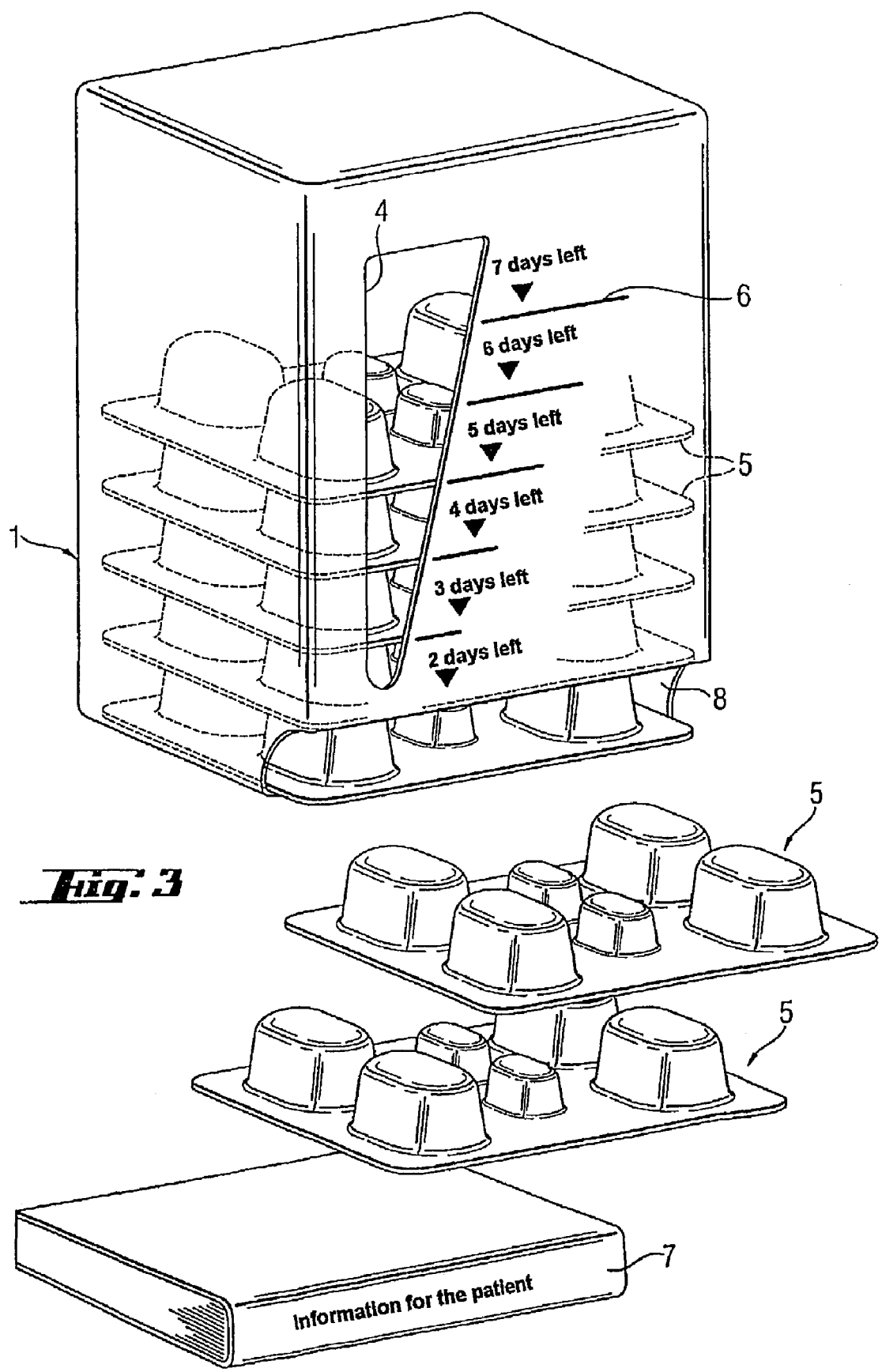

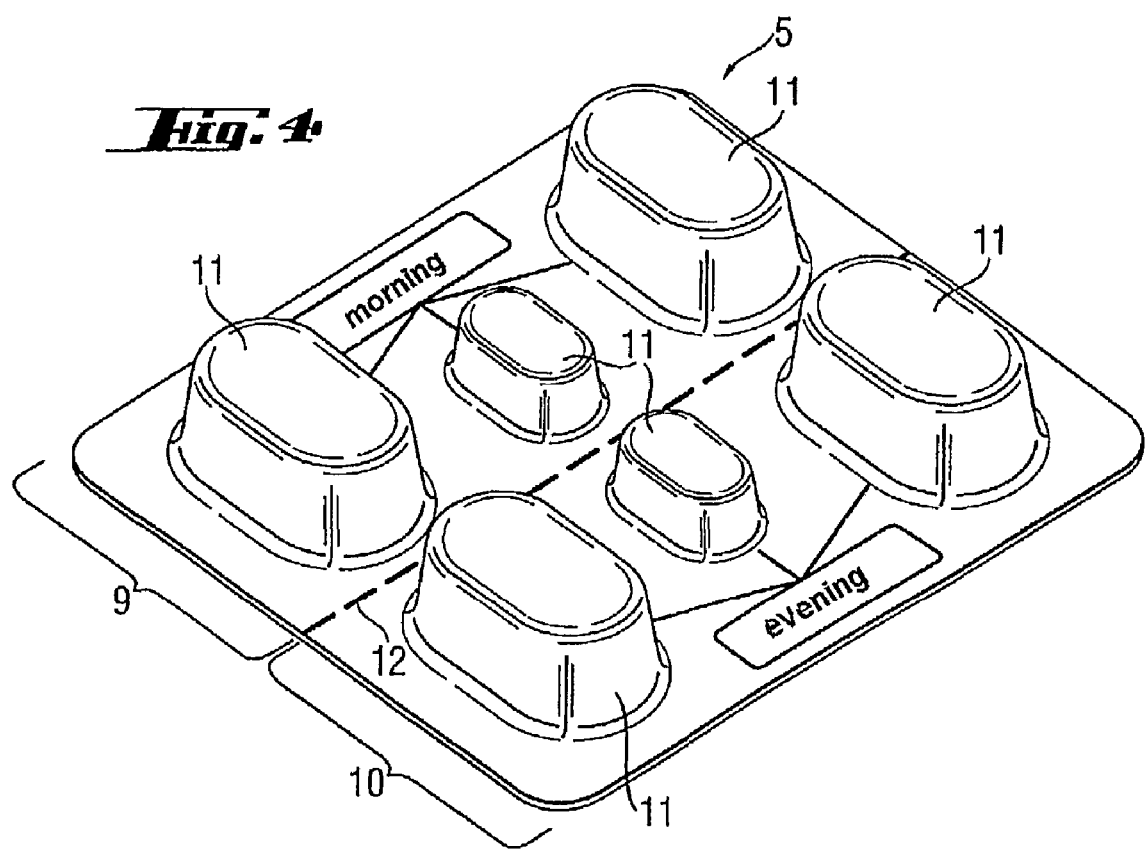

MEDICINAL PRODUCT PACKAGE FOR ERADICATION THERAPY

TECHNICAL FIELD

Figure 1:
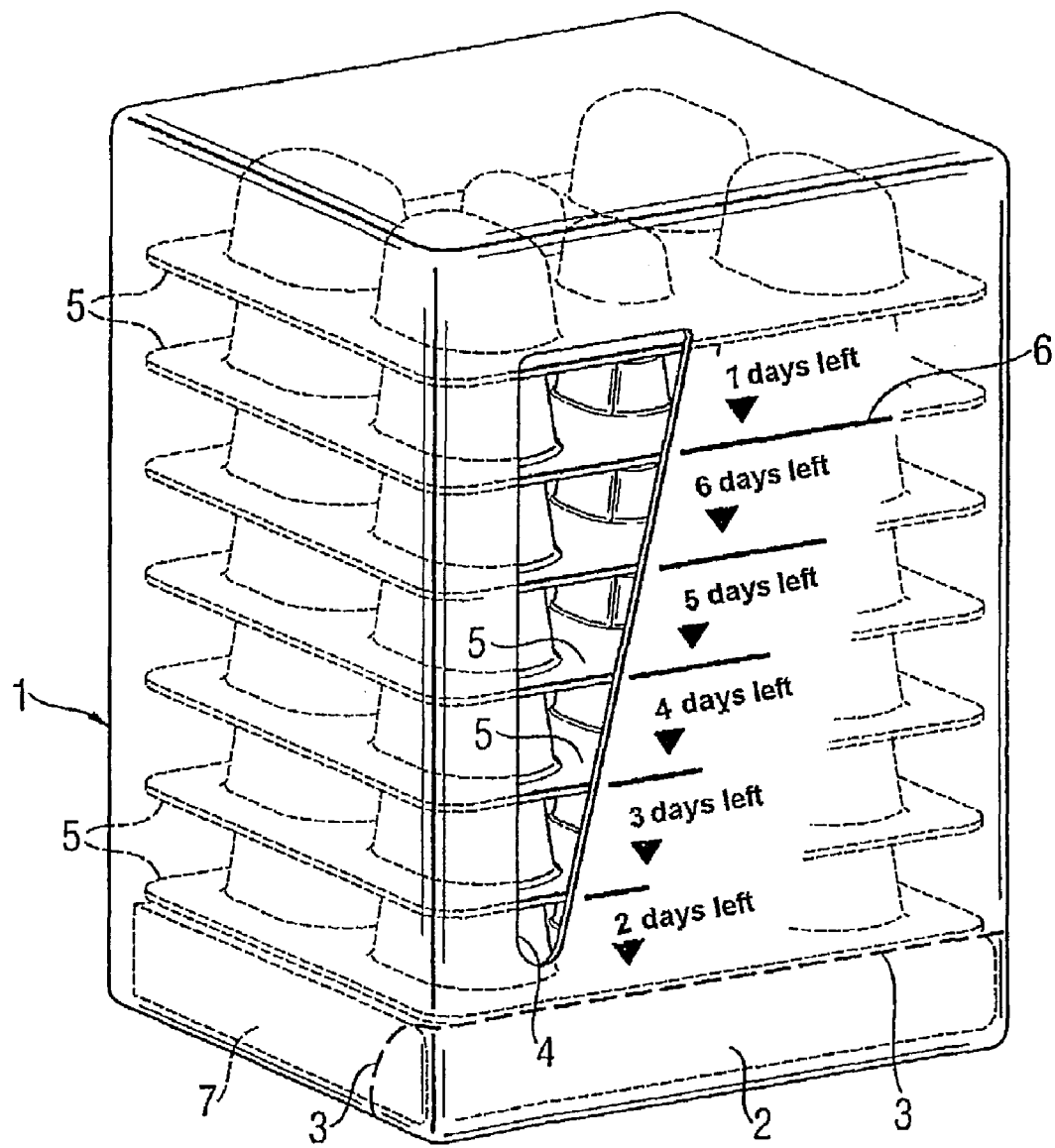

The present invention relates to a novel medicinal product package for housing blister cards for eradication therapy. Patient compliance can be noticeably increased with this package.

PRIOR ART

For the treatment of *Helicobacter pylori* disorders, the BDA (Professional association of general practitioners in Germany: Künzel D.; BDA-Leitfaden: Unklare Oberbauchbeschwerden; published by: Kybermed GmbH, Emsdetten, 1st edition, Emsdetten 1999) and the ESPCG (European Society for Primary Care Gastroenterology: Rubin G. P.; European Journal of General Practice, Vol. 5, 1999) recommend a combination therapy in which a proton pump inhibitor is administered at the same time as two different antibiotics. It is possible with such a triple therapy to achieve impressive eradication results (Huang J. Q., Hunt R. H.; GUT Vol. 45, Suppl. 1, 1999, i40).

The disadvantage of such a triple therapy is that, if the desired result of therapy is to be achieved, the patient has to swallow several tablets, often of considerable size, several times a day, normally two to three times. It is additionally necessary for intake generally to take place over a lengthy period of about seven to fourteen days. For successful treatment, a patient must show great compliance (adherence to therapy, i.e. compliance with a therapeutic instruction), and he must therefore adhere to the preset tablet composition and time of intake. Experience has shown that compliance by the patient is often less than expected without encouraging measures. Tablets are often taken at the wrong time, or intake is completely or partly forgotten, or the patient terminates the therapy before using all the tablets provided in the package. The risk of premature discontinuation of the therapy particularly applies to *Helicobacter pylori* therapy because there is a rapid improvement in the patient's wellbeing after the start of the therapy. The consequence of premature discontinuation of the therapy is, however, that complete eradication of the microbe is not achieved and, in addition, the microbe may develop resistance to the antibiotics used. Without measures for encouraging compliance, therefore, distinctly poorer results of therapy are to be expected.

EP-391 459 B1 describes a medicament package for improving compliance with a base in which a plurality of blister cards is stacked horizontally one on top of the other in a defined sequence, and with a lid which covers the base. The lid is movable into an open position whereby access to the uppermost blister card is provided. This makes it possible, in complex treatments, to avoid the patient taking a wrong blister card and consequently taking the wrong medicinal product at a given time.

DESCRIPTION OF THE INVENTION

The object of the present invention is to provide a medicinal product package which is suitable for microbe eradication therapy and with which the patient's compliance is increased and thus the result of therapy is improved.

This object is achieved by a medicinal product package where the package comprises: (a) a multiplicity of blister cards of generally uniform planar dimensions, where the blister cards are disposed in a stack with their principal dimensions oriented generally horizontally and arranged in order of card use, with the first card to be used lying right at the bottom and (b) a container which houses the stack of blister cards, where the container has an access for removing the blister lying right at the bottom, and where the container has means for indicating the remaining days of treatment as a function of the blister cards removed.

The use of the medicinal product package of the invention in microbe eradication therapy leads to distinctly increased compliance by the patient, and the package has proved to be particularly suitable in therapy for eradication of *Helicobacter pylori* using pantoprazole or other proton pump inhibitors such as, for example, omeprazole in combination with antibiotics.

The medicinal product package comprises a container whose shape and dimension is suitable for housing blister cards of the usual size. The container preferably has a shape customary for secondary medicinal product packages, for example the shape of a cuboid. The container is preferably fabricated from materials which are normally used for producing secondary medicinal product packages, such as, for example, paperboard. A multiplicity of blister cards is stacked one on top of the other oriented horizontally in the container. The container additionally has means for creating an access for removing the blister card lying right at the bottom of the stack of blister cards in each case. It is thus possible for the container to have, for example, first zones which can be detached from the remainder of the container. These first zones preferably have dimensions such that detachment thereof from the remainder of the container creates an opening through which, when the container is correctly oriented, only the blister card lying right at the bottom can be removed. With containers fabricated from a suitable paperboard, these first zones may comprise perforated marginal lines which make it possible easily to detach the first zones from the remainder of the container. The container additionally has means for indicating the remaining days of treatment depending on the number of removed blister cards. For this purpose, the container may have, for example, a second zone which makes it possible for a viewer to establish the number of days of treatment still remaining, as a function of the quantity of blister cards present in the package. For example, the second zone may be a vertically oriented; elongate, transparent zone in a side wall of the container. The transparent zone may be, for example, an opening. A scale with the number of days of treatment, as a function of the height of the stack of blister cards, is printed horizontally on the transparent zone or on the container adjacent to the elongate transparent zone. If all the blister cards are still present in the package, then the blister card lying uppermost in the container is located horizontally in line with the printed number which corresponds to the total number of days of treatment. After removal of a first blister card, the total height of the stack of blister cards is lower, and the topmost blister card is located horizontally in line with the printed number corresponding to the total number of days of treatment minus one. After removal of a second blister card, the total height of the stack of blister cards is lowered, and the topmost blister card is located horizontally in line with the printed number corresponding to the total number of days of treatment minus two etc. If required, a leaflet with information for the patient may also be located in the container underneath the stack of blister cards and must then, where appropriate, first be removed before the blister card lying right at the bottom can be removed. The container is fabricated in a conventional way familiar to the skilled worker.

The blister card can likewise be fabricated in a conventional way known to the skilled worker. Thus, for example, it is possible to insert between two base plates made of a suitable material, such as plastic or board, two other layers of material, one of which forms the blister cavities and the other forms the easily pierced blister base, or it is possible to choose a two-layer structure of the blister in which the cavities are incorporated into the upper layer and the latter is then coated from below with another layer of an easily pierced material, which closes the openings in which the medicaments are located.

The usual materials known to a skilled worker for producing commercially available blisters are used, such as, for example, laminated aluminum sheets, PVC (polyvinyl chloride) or PVdC (polyvinylidene chloride) sheets or combinations thereof or PP (polypropylene) sheets or combinations or laminations of said materials.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

The individual daily sections and, if required, the time of day sections can be detached from one another owing to perforation. The patient is thus able after removal of the medicaments to detach the corresponding section and obtain a more easily inspected blister card. This also reduces the probability of medicaments whose intake has been forgotten subsequently being taken, which may lead, for example, to unwanted high medicament concentrations.

The number of blister cards present in the medicinal product package of the invention depends on the duration of therapy and the number of medicaments to be taken. The number of blister cards is normally four to twenty, preferably seven to fourteen.

The medicinal product package can advantageously be employed in the therapy of *Helicobacter pylori* disorders. Preferably employed as active ingredients in such cases are proton pump inhibitors such as pantoprazole, omeprazole and other proton pump inhibitors known to the skilled worker in combination with antibiotics such as amoxicillin, clarithromycin, azithromycin, tetracycline, metronidazole and tinidazole. The proton pump inhibitor is moreover preferably combined with two different antibiotics (triple therapy). Examples which may be mentioned are combination of proton pump inhibitor with amoxicillin and clarithromycin, combination of proton pump inhibitor with clarithromycin and metronidazole, and combination with proton pump inhibitor with amoxicillin and metronidazole. The active ingredients are in these cases employed in the amount customary and necessary for the treatment. The therapy is normally carried out for a period of from seven to fourteen days.

The invention is now explained by means of the figures which show an exemplary embodiment of a medicinal product package of the invention employed for *Helicobacter pylori* therapy.

FIG. 1 shows a medicinal product package 1 of the invention made of paperboard in the closed state for a seven-day therapy for *Helicobacter pylori* eradication, employing as active ingredients pantoprazole in combination with amoxicillin and clarithromycin. The package 1 has a first zone 2 which is intended to be detached and is surrounded by a perforated line 3. As means for indicating the remaining days of treatment, the package has a vertically oriented elongate opening 4. Through the opening 4 it is possible for a viewer to see the seven blister cards 5 with the daily dose of the medicaments employed in the package 1. A scale 6 is printed on the container 1 in connection with the elongate opening 4 and indicates the remaining days of treatment as a function of the height of the stack of blister cards 5.

Figure 2:
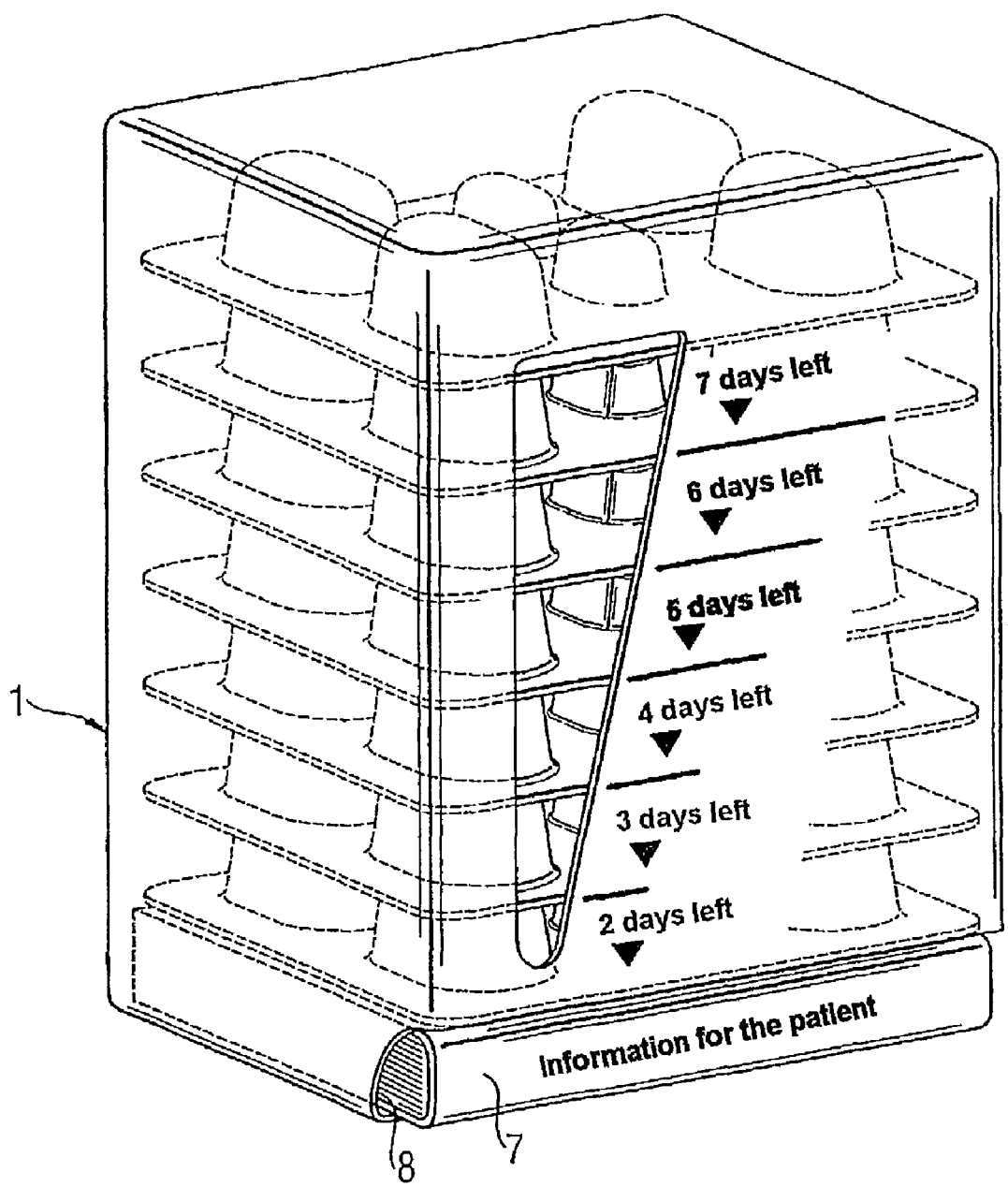
Figure 2:
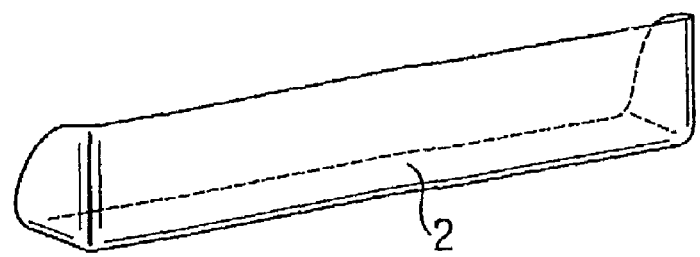

FIG. 2 shows the medicinal product package 1 after detachment of the first zone 2 along the perforated line 3. Underneath the stack of blister cards 5 there is a leaflet 7 with information for the patient, which is accessible through the removal opening 8 which has been produced.

FIG. 3 shows the medicinal product package 1 after removal of the leaflet 7 with the information for the patient and after removal of two blister cards 5. The stack of blister cards 5 still contains five blister cards for the remaining 5 days of treatment. The topmost blister card 5 in the stack is now in a horizontal location in line with the printed "5 days left".

FIG. 4 shows a blister card 5 for housing the daily dose of the medicaments employed. The blister card is divided into two time of day of sections 9, 10, the sections accommodating the medicaments to be taken in the morning and evening respectively. Each time of day section 9, 10 comprises three blister cavities 11 accommodating pantoprazole (40 mg), amoxicillin (1000 mg) and clarithromycin (500 mg).

The time of day sections 9, 10 are designed to be separable by a perforation 12.

What is claimed is:

1. A medicinal product package for improving compliance in microbe eradication therapy, where the package has: (a) a multiplicity of blister cards of generally uniform planar dimensions, where the blister cards are disposed in a stack with their principal dimensions oriented generally horizontally and arranged in order of card use, with the first card to be used lying right at the bottom; (b) a container which houses the stack of blister cards, where the container has an access for removing the blister card lying right at the bottom, and where the container has means for indicating the remaining days of treatment as a function of the blister cards removed; and (c) a leaflet with patient information located in the container under the stack of blister cards.

2. A medicinal product package as claimed in claim 1, where the access for removing the blister card lying right at the bottom is a first zone of the container which comprises a perforated line and can be detached from the remainder of the container.

3. A medicinal product package as claimed in claim 1, where the means for indicating the remaining days of treatment as a function of the blister cards removed is a vertically oriented elongate, transparent zone in a side wall of the container, and a scale with the number of days of treatment as a function of the height of the stack of blister cards is printed horizontally on the transparent zone or on the container adjacent to the elongate transparent zone.

4. A medicinal product package as claimed in claim 1, where at least one of the blister cards contains a daily dose of medicaments, and the medicaments are disposed in sections on at least one of the blister cards according to the time of day at which they must be taken.

5. A method of using the medicinal product packaging as claimed in claim 1 for controlling *Helicobacter pylori* comprising providing a therapeutically effective amount of pantoprazole and at least one antibiotic to a patient in need thereof, wherein the pantoprazole and the at least one antibiotic are provided in the medicinal product packaging as claimed in claim 1.

6. The method as claimed in claim 5, wherein the at least one antibiotic is selected from the group consisting of amoxicillin, clarithromycin, metronidazole, tinidazole, azithromycin, tetracycline and mixtures thereof.

7. A medicinal product package as claimed in claim 1, wherein the blister card contains at least one proton pump inhibitor in combination with at least one antibiotic.

8. A medicinal product package as claimed in claim 7, wherein said at least one proton pump inhibitor is selected from the group consisting of pantoprazole, omeprazole, and mixtures thereof.

9. A medicinal product package as claimed in claim 7, wherein said at least one antibiotic is selected from the group consisting of amoxicillin, clarithromycin, azithromycin, tetracycline, metronidazole, tinidazole, and mixtures thereof.

10. A medicinal product package as claimed in claim 7, wherein the blister card contains at least two antibiotics.

11. A medicinal product package as claimed in claim 1, wherein said leaflet must be removed from the container before said blister card lying right at the bottom can be removed.

12. A medicinal product package as claimed in claim 1, wherein four to twenty blister cards are present in said package.

13. A medicinal product package as claimed in claim 12, wherein seven to fourteen blister cards are present in said package.

* * * * *